United States Patent
Reiner et al.

(10) Patent No.: US 11,083,398 B2
(45) Date of Patent: Aug. 10, 2021

(54) METHODS AND SYSTEMS FOR DETERMINING MENTAL LOAD

(71) Applicant: NeuCogs Ltd., Haifa (IL)

(72) Inventors: Miriam Reiner, Haifa (IL); Shay Hilel, Tel-Mond (IL); Zeev Hadar, Tel-Mond (IL)

(73) Assignee: NeuCogs Ltd., Haifa (IL)

( * ) Notice: Subject to any disclaimer, the term of this patent is extended or adjusted under 35 U.S.C. 154(b) by 237 days.

(21) Appl. No.: 15/834,171

(22) Filed: Dec. 7, 2017

(65) Prior Publication Data

US 2019/0175090 A1 Jun. 13, 2019

(51) Int. Cl.
| | |
|---|---|
| A61B 5/16 | (2006.01) |
| G16H 20/70 | (2018.01) |
| A61B 5/369 | (2021.01) |
| A61B 5/00 | (2006.01) |
| A61B 5/024 | (2006.01) |
| A61B 5/0533 | (2021.01) |

(52) U.S. Cl.
CPC .............. *A61B 5/163* (2017.08); *A61B 5/165* (2013.01); *G16H 20/70* (2018.01); *A61B 5/0077* (2013.01); *A61B 5/02405* (2013.01); *A61B 5/0533* (2013.01); *A61B 5/369* (2021.01); *A61B 5/725* (2013.01); *A61B 5/7246* (2013.01); *A61B 5/7257* (2013.01); *A61B 5/7264* (2013.01)

(58) Field of Classification Search
CPC .................................................... A61B 5/163
USPC ........................................................ 434/236
See application file for complete search history.

(56) References Cited

U.S. PATENT DOCUMENTS

| | | |
|---|---|---|
| 2010/0292545 A1 | 11/2010 | Berka |
| 2011/0263946 A1 | 10/2011 | El Kaliouby et al. |

FOREIGN PATENT DOCUMENTS

| | | |
|---|---|---|
| WO | WO 2014/031758 | 2/2014 |
| WO | WO 2019/111259 | 6/2019 |

OTHER PUBLICATIONS

International Search Report and the Written Opinion dated Mar. 4, 2019 From the International Searching Authority Re. Application No. PCT/IL2018/051337. (21 Pages).

*Primary Examiner* — Kesha Frisby

(57) ABSTRACT

The present invention provides methods and systems for determining mental states of a user based on mental load index, comprising: analysing image data to identify feature(s) of at least one eye while presenting user with dynamic physiological-responsive stimuli; calculating, based on the identified feature(s), spatiotemporal fluctuations over time for the feature(s); calculating, based on the spatiotemporal fluctuations, spectral pattern(s) having a first and second frequency; calculating mental load pattern(s) by bounding ratio between the spectral patterns for the first and second frequencies in time interval(s) corresponding to stimuli level changes; identifying correlation between each mental load pattern(s) and the stimuli level in the time interval(s); and determining, based on the correlation, a mental load index comprising time interval(s) corresponding to a plurality of mental states identified by comparing each mental load pattern(s) to a threshold; and classifying mental state(s) based on the mental load index in each time interval(s).

34 Claims, 12 Drawing Sheets

METHODS AND SYSTEMS FOR DETERMINING MENTAL LOAD

FIELD AND BACKGROUND OF THE INVENTION

Some embodiments of the present invention, relate to methods and systems for generating a mental load of a user, and, more specifically, but not exclusively, to methods and systems for determining a mental load index and mental states of a user based on eye features analysis.

Eye tracking is used to monitor eye motion of a user by capturing image data during eye movement of a user and analyzing the location of the user's eyes. An optical eye tracker may use non-contact optical method for measuring eye motion, e.g., video-based eye trackers. Light may be reflected from the eye and sensed by a camera or other optical sensor to provide image data of eye movements. The image data is then analyzed to extract eye fluctuations from changes in the reflections.

Eye movements may be complex and may include various types of movements, including, fixation, gaze, saccades, convergence, rolling, pursuit, head movement, drift, pupil size, etc.

Monitoring of mental load is of great interest and importance in a variety of fields and applications, specifically, in evaluating effect of mental load on a worker's or operator's performance on a particular task or for evaluating users' responses.

SUMMARY OF THE INVENTION

According to some embodiments of some aspects of the present invention, there is provided a method for determining mental states of a user based on a mental load index. According to some embodiments, the method comprising: analysing image data to identify a plurality of features of at least one eye of a user while the user is presented with a dynamic physiological-responsive stimuli; calculating, based on the identified plurality of features, spatiotemporal fluctuations over time for each of the plurality of features; calculating, based on the spatiotemporal fluctuations, a plurality of spectral patterns having a first frequency and a second frequency; calculating a plurality of mental load patterns by bounding ratio between the spectral patterns for the first and second frequencies in a plurality of time intervals corresponding to changes in a level of the stimuli; identifying a correlation between each of the plurality of mental load patterns and the stimuli level in each of the plurality of time intervals; and determining, based on the correlation, a mental load index comprising a plurality of time intervals corresponding to a plurality of mental states, each state identified by comparing each of the mental load patterns to a threshold; and classifying at least one mental state of a user based on the mental load index in each of the time intervals.

According to some embodiments, the plurality of features is at least one of: fixation, duration of fixation, response time, saccades and microsaccades characteristics, latency in saccade/microsaccades response to stimuli, eye dynamics, pupil diameter and/or area variation, blink duration and blink rate.

According to some embodiments, the calculating spatiotemporal fluctuations step comprises integrating weight corresponding to at least one of the plurality of features selected from: fixation, saccade characteristics, saccade response time, duration, drift and response time of drift.

According to some embodiments, the image data is obtained by an imaging device selected from: a camera, smartphone, eye tracker and sonic source.

According to some embodiments, the image data is obtained from a distance between the imaging device and the user's eye of between about 1 cm and about 500 cm.

According to some embodiments, the distance is between about 1 cm and about 10 cm.

According to some embodiments, the calculating spectral patterns step comprises at least one analysis technique or algorithm selected from: clustering algorithm, changes in eye blinks, artifacts removal, wavelet denoising, regression, smoothing algorithm, Fourier Transform Function (FTF) and Kalman filtering.

According to some embodiments, the artifacts removal is carried out by at least one of data filtering algorithm and data validation.

According to some embodiments, the spatiotemporal fluctuations are further analysed by at least one average smoothing method and/or algorithm selected from:

(i) Fourier Transform Function (FTF) for replacing each data point on each of the first frequency and the second frequency with a predefined average of neighbouring data points to evaluate average intensity of each data point;

(ii) Discrete Fourier transform (DFT) for converting spatiotemporal data to relative frequency data; and (iii) Prime-factor FFT algorithm for calculating frequency data to provide spectral patterns respective to the plurality of ratio patterns of the low frequencies and the high frequencies.

According to some embodiments, the identifying a correlation step comprises assigning each point on each of the spectral patterns to at least one cluster based on similarity features to other points in the spectral patterns selected from: distance, connectivity, intensity characteristics and duration.

According to some embodiments, the assigning each point to at least one cluster comprises fuzzy c-mean clustering.

According to some embodiments, the calculating the mental load pattern is carried out at time intervals of between about 10 sec and about 60 sec.

According to some embodiments, the time intervals are between about 20 sec and about 40 sec.

According to some embodiments, the first frequency is between about 0.02 Hz and about 0.3 Hz and second frequency is between about between about 0.3 Hz and about 1 Hz.

According to some embodiments, the first frequency is between about 0.03 Hz and about 0.15 Hz.

According to some embodiments, the first frequency is between about 0.04 Hz and about 0.15 Hz.

According to some embodiments, the second frequency is between about 0.15 Hz and about 0.80 Hz.

According to some embodiments, the second frequency is between about 0.15 Hz and about 0.50 Hz.

According to some embodiments, each of the mental load patterns is characterized by a dependence which comprises a n-base logarithmic relation between a ratio of the first and the second frequencies, wherein n is between 2 and 10.

According to some embodiments, each of the mental load patterns is characterized by a dependence mathematically expressed as $MI=\log_n(LF/HF)$, where MI is the Mental Index, LF is the area bounded by the spectral pattern and the first frequency axis and the area bounded by the spectral pattern and the second frequency axis.

According to some embodiments, the at least one behavioural-responsive stimuli is one or more of: queries provided to a user by a virtual agent, and/or an interactive agent and/or a video.

According to some embodiments, the defining the mental load index is by comparing a mental load pattern in a first time duration to a baseline mental load having a threshold corresponding to another time duration characterized by presenting no stimuli or a generally low responsive stimuli to a user.

According to some embodiments, the step of identifying a correlation comprises identifying one or more of a start time, an end time or a time duration of each of the plurality of stimuli.

According to some embodiments, the identifying one or more of the start time, end time and time duration of each of the plurality of stimuli is based on obtaining an emotional feedback from a user to each stimuli.

According to some embodiments, the obtaining the feedback is by recording the user's output to mental load level respective to each of the stimuli by one or more of the techniques: a questionnaire comprising feedback questions, heart rate variability (HRV), heart rate (HR), galvanic skin response (GSR), changes in frequencies of facial colors, and EEG.

According to some embodiments, the method further comprises using the mental load index as a feedback for training to determine a mental state of a user in response to a stimuli by correlating between the trained feedback mental load and the mental load of the user.

According to some embodiments, the method does not include a calibration step.

According to some embodiments, the method further comprises calculating changes in response time of the user to each of the plurality of stimuli.

According to some embodiments, the at least one mental state is selected from disengaged, calm, interested, and stressed.

According to some embodiments of some aspects of the present invention, there is provided a system. According to some embodiments, the system comprising: at least one imaging device for analysing image data to identify a plurality of features of at least one eye of a user while the user is presented with a dynamic physiological-responsive stimuli; and at least one processor for: calculating, based on the spatiotemporal fluctuations, a plurality of spectral patterns having a first frequency and a second frequency; calculating a mental load pattern by bounding ration between the spectral patterns for the first and second frequencies in a plurality of time intervals corresponding to changes in a level of the stimuli; identifying a correlation between the mental load patterns and the stimuli level in each of the plurality of time intervals; and defining, based on the correlation, a mental load index by comparing each of the mental load patterns to a threshold respective to a plurality of mental states; and determining at least one mental state of a user respective to a plurality of stimuli based on the mental load index.

According to some embodiments, the at least one imaging device is selected from: a camera, a tv, a mobile device, an eye tracker, an IR source, and a sonic source.

According to some embodiments, the system further comprising a display for displaying data obtained from the processor.

According to some embodiments, the system further comprising a classifier for classifying at least one mental state based on comparing the mental load index obtained from the processor, to stored mental load data.

According to some embodiments, the system further comprising a controller for controlling access to a device being operated by the user, based on an output determined by the classifier.

According to some embodiments, the system wherein the imaging device and the processor, and optionally, one or more of the display, the controller and the classifier are embedded in a single device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of some embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
FIG. 1 is a flowchart of an exemplary method of determining a mental state of a user, according to some embodiments of the present invention.

Some embodiments of the present invention, relate to methods and systems for generating a mental load of a user, and, more specifically, but not exclusively, to methods and systems for determining a mental load index and mental states of a user based on eye features analysis.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments and/or of being practiced and/or carried out in various ways.

Mental Load refers to a measure of cognitive and/or physiological and/or emotional resources an individual devotes to responding to a stimulus (e.g., a task). As such, not only mental resources affect the mental load of an individual, other affects, including physiological and/or psychological effects, such as stress and fatigue, can influence an amount of mental resources a person devotes to a task. Subjective and objective tools can be used for mental load monitoring. Subjective load assessment typically involves participants completing a questionnaire every set of stimuli and/or every set of time, which can provide a mental load index by using subjective features rating that can then be combined into a single general mental load index. However, subjective load assessment lacks temporal resolution, as rapid changes in load need to be captured, whilst operator feedback is required at small intervals, which can increase load.

Physiological analysis techniques, such as electrocardiography (ECG), respiration, heart rate variability (HRV), eye tracking and electroencephalography (EEG) can offer continuous objective measurement of mental load to some extent. However, these techniques require signal corrections and high reaction times, and are highly sensitive to movement and/or muscle artifacts, and as such, generally influence readings of the physiological analysis techniques. Existing enhancement algorithms rely on dense electrode montages (e.g., 32 electrodes in EEG). In addition, specific aspects of mental load require different tasks to be used. Given the increased sensitivity of existing techniques and devices to noise and artifacts, it is highly desired to accurately capture load levels whilst providing robustness against lower quality neurophysiological signal readings.

Generally, methods used for analysing mental load pupil indicators are based on pupil dilation (PD). Changes in PD can be correlated with changes in mental states. However, such pupil analysis methods may include increased noise due to effects of light on dilation of the pupil and are typically inaccurate and inefficient. Signal due to flux change in light intensity is a magnitude higher than mental load signals and thus mental load analysis may be inaccurate and may cause mental load signals to be lost in the light signal. As such, linking between mental states of an individual responsive to a stimulus is typically inaccurate and inefficient.

Additionally, previous approaches provided an average measurement of mental load over a period of time of task performance, however, such methods have been found to be generally ineffective, as stress can be caused by a variety of factors that are unrelated to a task being performed. An additional drawback is that such measurements only measure the user's present state and cannot isolate the level of difficulty that the user is experiencing from other external factors, such as a lack of sleep. Use of the mental load index as determined according to some embodiments of the invention (e.g., by calculating spatiotemporal fluctuations over time for a plurality of eye features and based on the correlation step utilized according to some embodiments, an accurate relationship with the actual response of a user to a stimulus (e.g., performance of a task) is less affected by external factors than the methods and systems used in prior art.

Eye features, for example, pupil diameter may be monitored during picture viewing to assess effects of emotionally arousing images on pupillary responses associated with sympathetic and/or parasympathetic activity of the nervous system. Without wishing to be bound by theory, it was found that fluctuations in pupil diameter during image viewing may covary with changes in skin conductance, which may be supported by sympathetic nervous system activity, and which may provide support that pupil's response during effective picture viewing reflects emotional arousal associated with increased sympathetic activity.

Some embodiments of some aspects of the present invention provide methods and systems for accurately and efficiently determining mental state(s) of a user in response to one or more psychological and/or emotional and/or mental stimuli (e.g., event, task, etc.), by correlating between mental load pattern(s) (e.g., mental load intensity vs. time) derived from analysis of fluctuations in one or more eye feature(s) (e.g., pupil diameter, gaze position, pupil response time etc.) associated with changes over time in one or more physiological-responsive dynamic stimuli in respective time interval(s). Measuring the mental load of a user over time over a plurality of time intervals, according to some embodiments of the invention, provides determining user response dynamics (e.g., varying quantity—user performance difficulty level, and/or varying quality—different stimuli type, etc.) based on spatiotemporal fluctuations over time of eye features. The spatiotemporal fluctuations of the eye features over time can be utilized to calculate (or compute) a plurality spectral patterns (e.g., power spectrum densities—PSD) having a first frequency and a second frequency.

Some embodiments of the present invention utilize mental load pattern(s) calculated from the plurality of spectral patterns for frequencies corresponding to spatiotemporal fluctuations in the one or more eye feature(s) over time.

Each of the eye features can be identified from image data recorded by monitoring at least one eye of a user (e.g., via an RGB camera, IR camera, an eye tracker, etc.) while presenting the user with one or more dynamic stimuli over time. Previous approaches provided an average measurement of mental load over a period of time of task performance. In contrast to prior art, some embodiments of the invention provide engaging the user with dynamic stimuli as it changes over time and variations in the mental load over that time period are measured (or computed or calculated). For instance, a performance task is provided to an individual over a time period which gradually changes its difficulty level (or varying difficulty level), optionally in time intervals, and the changes in mental load over time is measured to obtain a plurality of mental load patterns. The mental load pattern(s) are then correlated to time intervals associated with each stimulus (e.g., stimulus level, difficulty) to generate a real-time, event-related mental load index for a plurality of mental states. In contrast to prior art, some embodiments of the invention provide identification and evaluation of changes in mental load patterns during real-time of the dynamic stimuli, with a high temporal resolution, and correlating between the mental load patterns and dynamic stimuli level (e.g., difficulty) in real time.

Previous techniques have attempted to use stress measurements in order to determine both performance quality and user difficulty level. Such methods have been found to be generally ineffective, as stress can be caused by a variety of factors that are unrelated to the task being performed. However, a drawback is that such measurements only measure the operator's present state and cannot isolate the level of difficulty that the operator is experiencing from other external factors, such as a lack of sleep the night before performing the task. Use of mental load index determined according to some embodiments of the invention, (e.g., by calculating spatiotemporal fluctuations over time for a plurality of eye features and using a baseline mental load (threshold) for correlating mental load to stimulus level), has an accurate relationship with the actual response of a user to a stimulus (performance of a task) and is less affected by external factors than the methods and systems used in the prior art.

Some embodiments of the invention provide identifying one or more mental load peak thresholds (e.g., of difficulty), and as such, different users having different attributes (e.g., skill levels) can be identified, by determining time periods where each user experiences an increased performance level (e.g., difficulty) in performing various stimulus types.

This may be utilized to provide evaluation of a user's ability to perform a task, and conditions for optimal performance for each individual. Additionally or alternatively, mental load measurements for a particular stimulus and/or a particular user can be compared to mental load measurements for the same user engaged in different stimuli. Additionally or alternatively, some embodiments provide accurately evaluating if a particular user is suited to perform a particular stimulus, optionally, in particular situations. Thus, some embodiments of the invention provide measuring performance quality and/or user difficulty level.

Additionally or alternatively, the mental load index data can be used to create a mental load profile of a user. Optionally, the mental load profile can be used to determine a functional limit when undergoing a particular mental load for a stimulus (e.g., a task) being performed by the user.

Methods of the art do not take into account changing quality of mental load in transitions between different load levels. Some embodiments of the present invention utilize the mental load index for determining various useful indications. For instance, the mental load index provided according to some embodiments of the invention, can measure user performance level in simulators and/or in actual conditions by comparing the mental load of user performance with baseline values (e.g., above/below a threshold, determined according to some embodiments as described below).

The mental load index according to some embodiments of the present invention can be utilized to classify a plurality of mental states of a user by comparing each mental load level in the mental load index to a threshold level for a defined stimulus. Some embodiments of the present invention utilize a baseline mental load level for defining a threshold level associated with at least one reference stimulus, e.g., before onset of a stimulus and/or during a stimulus having a generally low mental load level (for example, a relaxing video). Some embodiments of the invention provide a mental load index by comparing a mental load pattern of a first time duration to a baseline mental load corresponding to a second time duration and characterized by presenting no stimulus and/or a generally low responsive (e.g., eye response) stimulus to a user.

Some embodiments of the present invention utilize a plurality of threshold mental load levels for determining each mental state of a user (e.g., calm, disengaged, highly engaged, interested, etc.). Each mental state can be identified by comparing each mental load pattern to each threshold level (best match and/or above a defined threshold) that corresponds to the mental load in response to a given stimulus. Some embodiments provide identifying a correlation of one or more mental load patterns with each stimulus in corresponding time intervals, including, for example, identifying one or more of a start time, an end time and/or time duration for each stimulus. Optionally, the identifying one or more of the start time, end time and/or time duration is based on obtaining an emotional feedback from a user to each stimulus (e.g., by gathering feedback from the user of an actual real specific emotional response during the stimuli, for example, by receiving user's response via a questionnaire). Further optionally, the emotional feedback can be provided by recording the user's output to mental load level respective to each stimulus by one or more of the techniques: a questionnaire comprising feedback questions, heart rate variability (HRV), heart rate (HR), galvanic skin response (GSR), changes in frequencies of facial colours, and/or electroencephalography (EEG).

The stimulus can be ongoing, e.g., one or more stimuli presented to the user continuously and/or in intervals, and mental load responses of the user are recorded over time from the user's eyes. Mental load may be obtained, according to some embodiments of the invention, by analysing spectral patterns in a plurality of frequency ranges (e.g., by dividing spectral patterns in a first frequency and in a second frequency to obtain a ratio designated herein: LH). Some embodiments utilize analyzing the LH value in a plurality of time intervals.

Mental Load Index may be utilized to determine mental states of a user in response to a dynamic stimulus as it changes over time in time intervals. Such mental states of a user may include, for example, cognitive and/or physiological and/or emotional states, in particular, disengagement (e.g., user non-attentive), calm and/or minimally engaged, highly engaged and/or interested, stress, frustration, etc. The mental load index is a measure of an individual user's response and/or multiple users' response to a certain stimulus and typical ranges of mental load intensity may be developed for certain stimulus. Based on the unique mental load index provided according to some embodiments of the invention, a plurality of mental states of a user can be accurately and efficiently classified by correlating between mental load patterns and a dynamic stimuli in identified time intervals, and comparing each of the mental load patterns (e.g., continuous pattern of mental load intensity vs. time having a plurality of segments) to a threshold mental load for each of the plurality of mental states of a user. Each segment of mental load is paired to a defined stimulus at corresponding time intervals, e.g., varying from generally low to generally high mental load (for example, from every easy to very hard performance task). Each pair of mental load level and stimulus may be correlated to a mental state according to being above and/or below a defined threshold.

It is an aim of some embodiments of the invention to provide accurate capturing and/or measuring of mental load levels whilst providing robust high quality signal readings analysis and to provide accurate identification of each mental and/or emotional state of an individual.

Some embodiments of the present invention provide accurate identification of spatiotemporal fluctuations in eye features of a user that are obtained from image data by monitoring a user's eye(s) and acquiring eye image data, for example, via an imaging device (e.g., position and/or time of eye features of a user).

Some embodiments of the present invention are described herein with reference to flowchart illustrations according to some embodiments of the invention. It will be understood that each block of the flowchart illustrations and/or block diagrams, and combinations of blocks in the flowchart illustrations, can be implemented by computer readable program instructions. The flowcharts in the Figures illustrate the architecture, functionality, and operation of possible implementations of methods and/or systems according to some embodiments of the present invention.

Some embodiments of the present invention can be implemented in software, and/or in hardware, and specifically in a combination thereof. Methods according to some embodiments of the present invention can be performed by software according to some embodiments of the present invention, or stored on a computer-readable medium, when executed, performs one or more of the steps of the methods.

Figure 2:
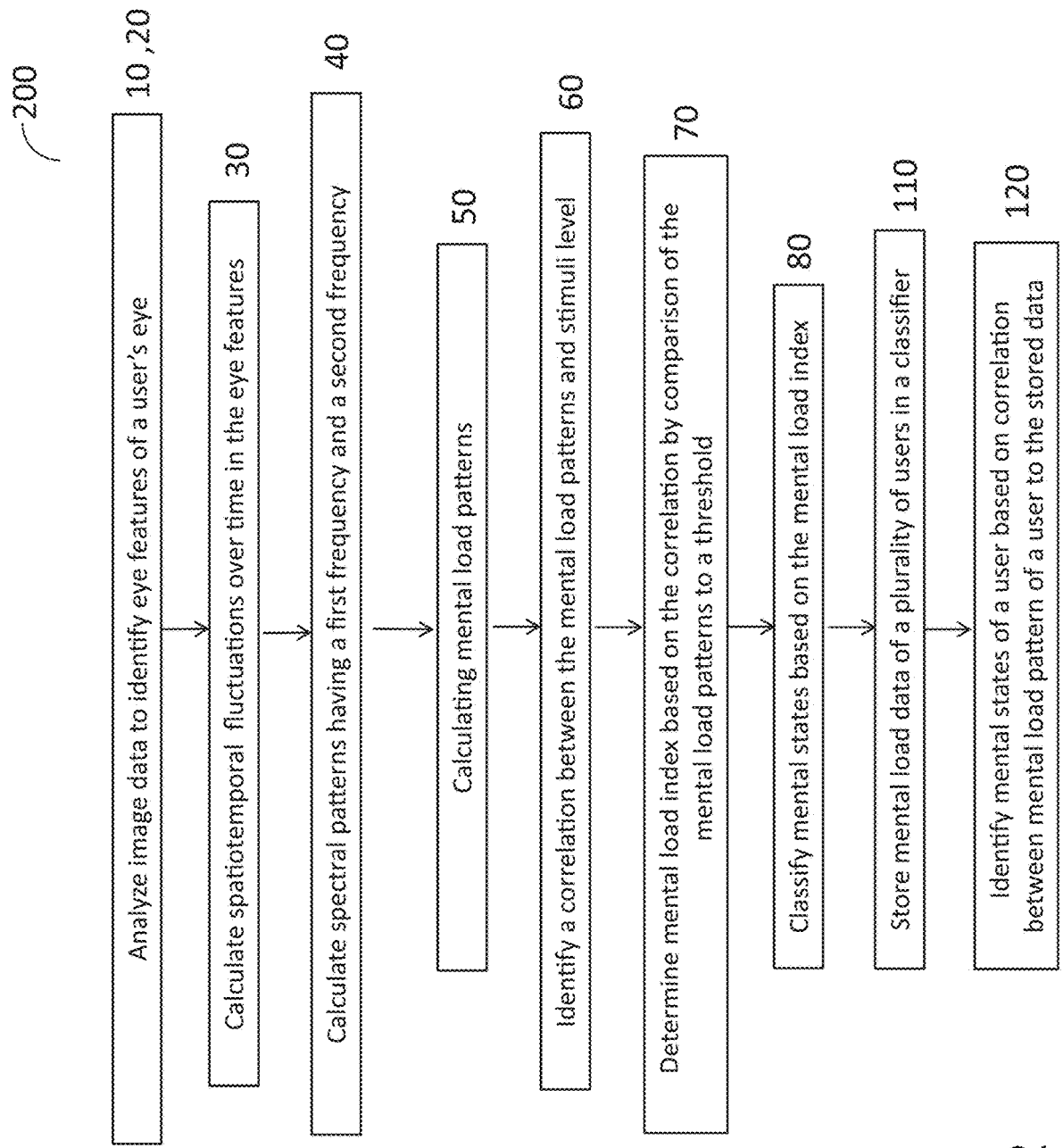
FIG. 2 is a flowchart of an exemplary method of correlating between a mental state and physiological-responsive stimuli based on a mental load index, according to some embodiments of the present invention.
Figure 3A:
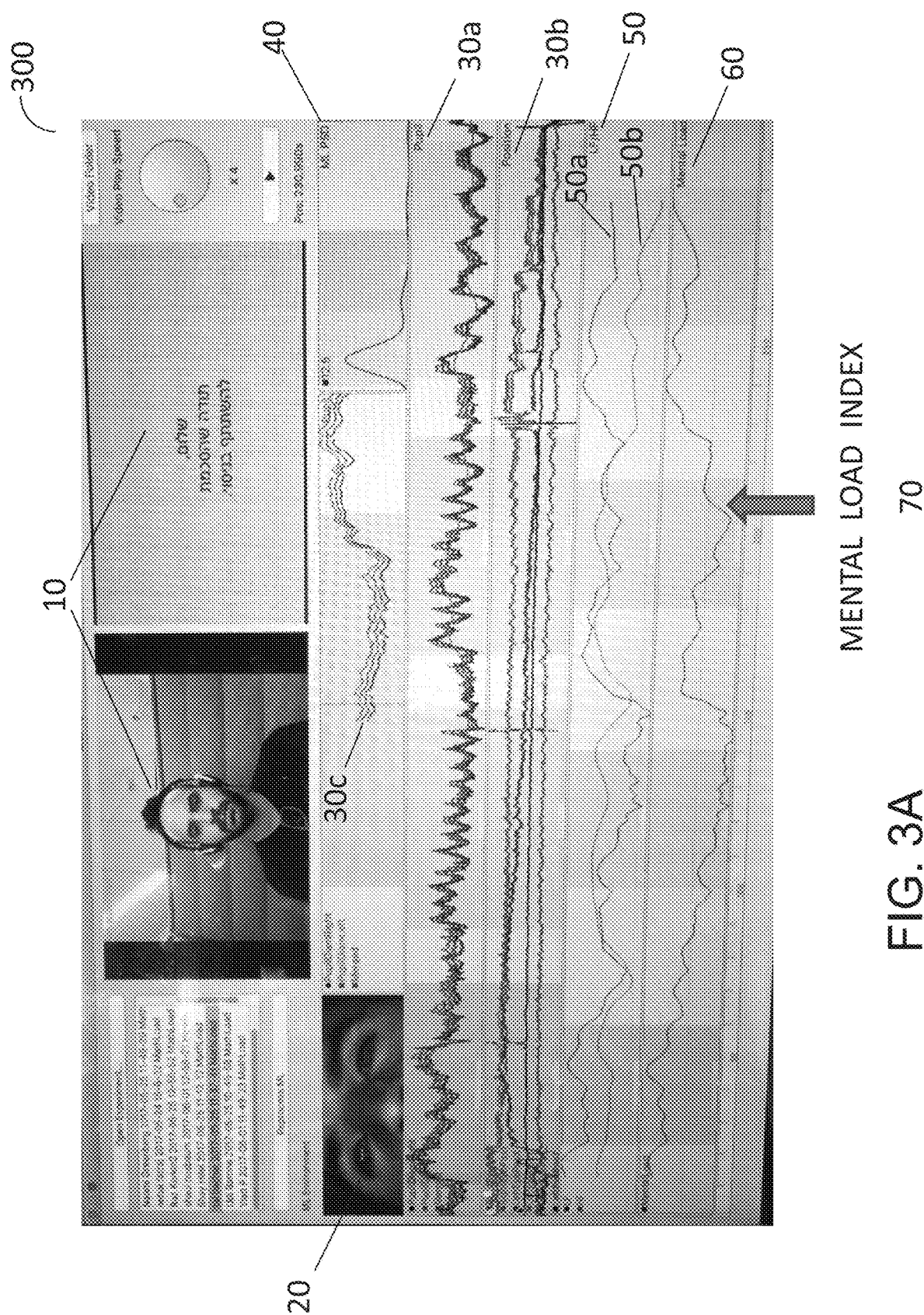
FIGS. 3A-3B are screen shots of a display showing an illustration of data recorded from eye features in two exemplary experiments and analysis thereof, according to some embodiments of the present invention.
Figure 3B:
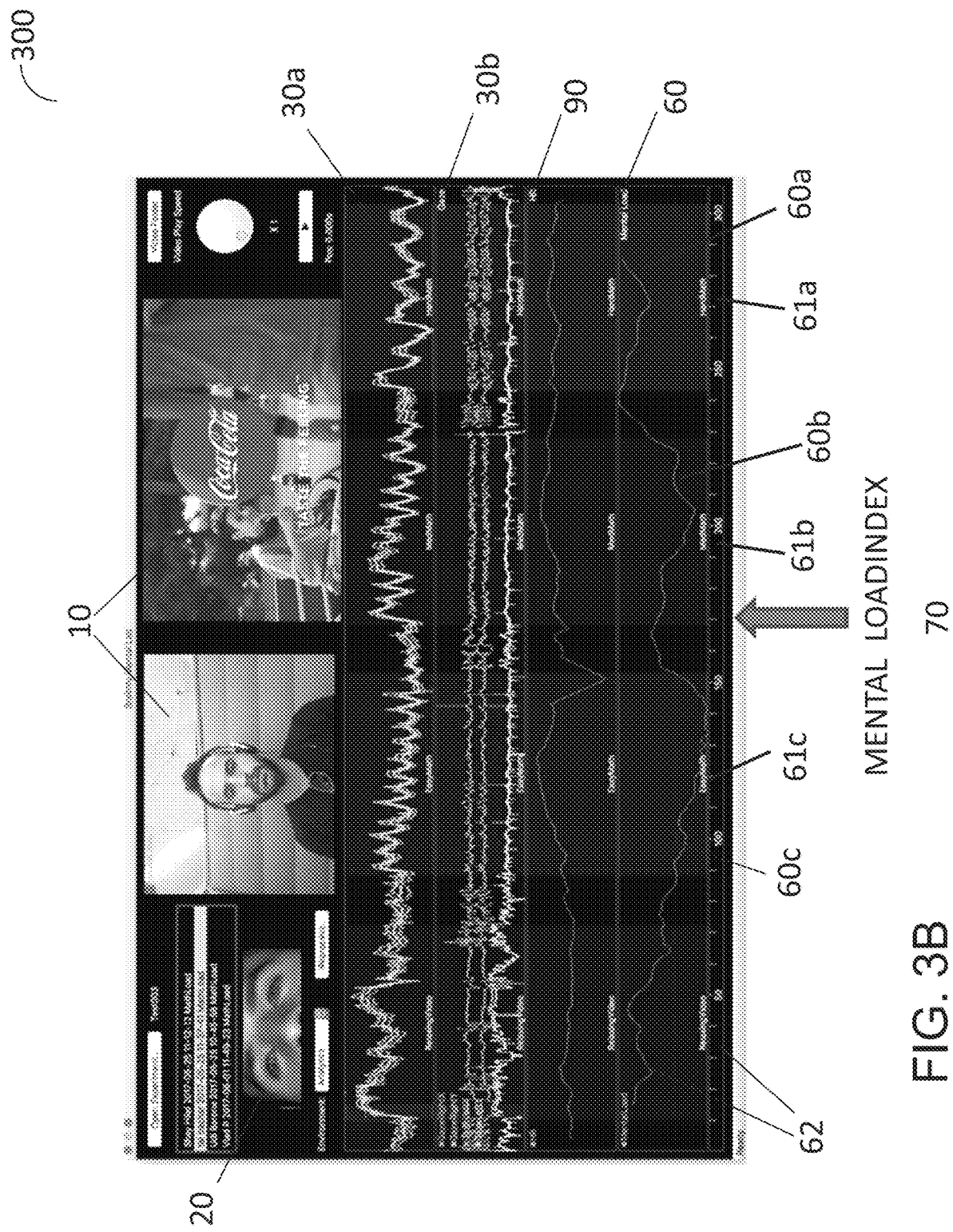

Reference is now made to FIG. 1, which represents a flowchart of an exemplary method of determining a mental load index of a user 100, according to some embodiments of the present invention. Reference is also made to FIG. 2, which presents a flowchart of an exemplary method of identifying mental states of a user by using a mental load index 200, according to some embodiments of the present invention. Reference is also made to concomitantly to FIGS. 3A-3B, which represent graphical illustrations of some method steps involved in an exemplary experiment, according to some embodiments of the present invention.

Each of the flowcharts depicted in FIGS. 1-3B, may be executed consecutively for continuously obtaining image data of eye features of a user and/or for processing (calculating or computing or analyzing or determining or identifying) the data to provide a mental load index of a user.

Methods 100, 200, 300, 400 according to some embodiments of some aspects of the present invention, utilize identifying a plurality of features 20 of at least one eye of a user in response to changes in one or more stimulus 10 presented to the user. One or more of the eyes of a user are monitored to obtain baseline data 62 of a plurality of eye features (e.g., image data prior to providing the user with a stimulus, or during a low level stimulus—relaxing stimulus). As the stimulus is being provided to the user the plurality of eye features of the user are further captured. Spatiotemporal fluctuations over time in the eye features are then calculated to provide a pattern of fluctuations in each of the eye's features (e.g., in position and time) 30, 40. Spectral patterns (e.g., Power Spectra Density—PSD) in a first frequency and a second frequency 50 are calculated from the pattern of spatiotemporal eye fluctuations 30, 40 (e.g., by transforming the data from a time domain to a frequency domain). Then the spectral patterns 50 are analysed to calculate a plurality of mental load patterns 70 by bounding ration between the spectral patterns for the first and second frequencies in a plurality of time intervals corresponding to changes in a level of the stimuli 60 (e.g., pattern of mental load vs. time). A correlation between each of the plurality of mental load patterns 70a-70c and the stimuli level 71a-71c in each of the plurality of time intervals are identified (e.g., Dynamical Mental Load). Based on the correlation, a mental load index 80 is determined. The mental load index 80 comprises a plurality of time intervals corresponding to a plurality of mental states, each state identified by comparing each of the mental load patterns 70a-70c to a threshold 72. At least one mental state of a user is classified based on the mental load index 80 in each of the time intervals 90. The methods of the invention can include one or more optional steps of receiving eye movement data, and/or eye monitoring, and/or eye movement detection, and/or blink detection, and/or storing data in a memory, and/or further calculating and/or computing steps, such as, smoothing and/or filter steps to remove noise. The method can further include an optional step of using the determined mental load index as feedback, optionally, for training.

Some embodiments of some aspects of the invention provide utilizing a mental load index 80 as determined herein for identifying (or predicting) a mental state of one or more users in response to one or more stimulus. The mental load data of a plurality of users can be stored in a classifier 110. Mental states of a user can be identified based on correlation between mental load patterns of a user to the stored data 120. The stored mental load data can include average and/or instantaneous mental load measurements for a particular stimulus, measurements for a particular user and/or group of users, and/or event-related mental load, and/or any other type of mental load data, as can be appreciated by one of skill in the art. Output data resulting from the classification step can be further provided to a display.

Some embodiments of the present invention can also be used in order to prevent access to a particular task and/or device if a user's mental load measurement is found to be exceeding a particular threshold, e.g, as stored in a classifier. The mental load measurement from the classifier can be provided to a controller, which can selectively restrict access for an operator based on the comparison of the measured load to a threshold value. The threshold can be a general threshold for all users and/or can be a personalized threshold for the particular user. The threshold can be stored in a memory within a controller, and/or any memory external to the controller.

The mental load index can further be used as a feedback for performing, and/or training, and/or learning task (e.g., solving a problem in physics, performing surgery, etc.) to determine a mental state of a user in response to the task by correlating between the task and changes in the mental load of a user during performance of the task.

Figure 11:
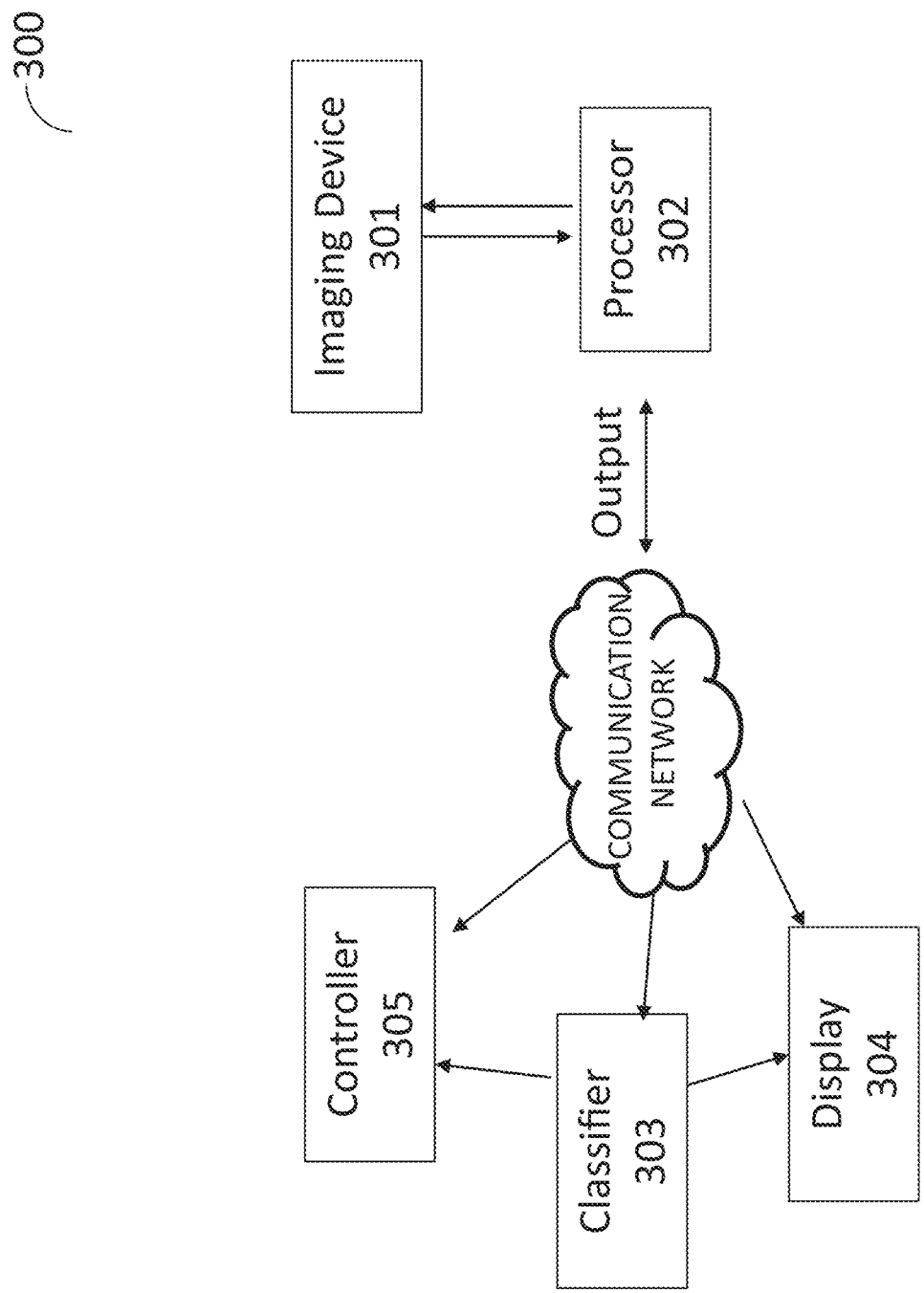
FIG. 11 is a schematic illustration of an exemplary system for determining a mental state of a user, according to some embodiments of the present invention.

Reference is now made to FIG. 11, which is a schematic illustration of an exemplary system 300 for determining a mental state of a user, according to some embodiments of the present invention.

System 300 includes an imaging device 301 (e.g. a camera, eye tracking device, etc.) for identifying one or more eye features from the user's eyes while the user is presented with dynamic physiological-responsive stimuli. One or more eye features that may be responsive to a stimuli according to some embodiments of the invention, include, for example, fixation, duration of fixation, response time, gaze, saccades and/or micro-saccades, latency in saccade and/or microsaccades, convergence, rolling, pursuit, nystagmus, drift, physiological nystagmus, blinking duration, blinking rate, pupil size (e.g., pupil diameter, pupil area variation), pupil area variation due to head movements and/or the like.

Imaging device 301 may be connected to the system 300 through an interconnection (and/or may share the interconnection) and optionally comprising at least one interface and/or at least one network server. The interface may include at least one wired and/or wireless interface, for connecting to the interconnection to communicate with the imaging device 303.

Then, the image data is recorded and transmitted to a processor 302, for processing the image data, e.g., via a wireless connection. Processor 302 may also be utilized for executing one or more additional method steps according to some embodiments of the invention.

In some embodiments, one or more of the data determined according to one or more steps of the method of the invention, particularly, mental load data is provided in real time as feedback (output data) in the system 300 as shown in FIG. 11. Some embodiments utilize a classifier 303 for classifying at least one mental state based on comparing the mental load index obtained from the processor, optionally, to stored mental load data. The classifier can itself include simulation/evaluation software. The stored mental load data can include average and/or instantaneous mental load measurements (e.g., short term responses taken within 250 to 1250 ms (milliseconds), or even within 250 to 3000 ms) for a particular stimulus, measurements for a particular user or group of users, or any other type of mental load data, as can be appreciated by one of skill in the art. The output data resulting from the processing in the classifier can be provided to a display 304, such as a video display.

Yet further additionally, some embodiments of the present invention utilize a display 304 for providing output data, optionally obtained from the processor. The display 304 can show one or more data and/or patterns determined and/or calculated according to some embodiments of the invention, including, spatiotemporal fluctuations over time for each of the eye features in real time, and/or spectral data, and/or mental load data and/or stimuli data. The display can be used in particular for showing feedback, e.g., for training a user (autonomous training). The feedback data regarding mental load determined according to some embodiments of the invention can be displayed to the user himself. Alternatively, the display data can be optionally provided to a third person who is observing the training, and can later be provided to the user.

Some embodiments of the present invention utilize a real-time, low latency processor 302, that may graphically present output of the level of user mental load (e.g., stress) and/or other responses while processing a stimuli. The real-time output may be stored and/or may be used to provide feedback to the user, and/or to an external intelligent system controller 305, e.g., for decision making.

Yet further additionally, some embodiments of the present invention utilize a controller 305 for controlling access to a device being operated by the user, based on an output determined by the classifier 303. The output of the classifier can also be provided to a controller. In some embodiments, the imaging device and the processor, and optionally, one or more of the display 305, the controller 304 and the classifier 303 are embedded in a single device.

Components of the system 300 may be connected to the system 300 through an interconnection (and/or may share the interconnection) and optionally comprising at least one interface and/or at least one network server, via, e.g., at least one wired and/or wireless interface, for connecting to the interconnection to communicate with the components of the system 300.

Software that can be used with the methods and systems according to some embodiments of the present invention, are designed for analyzing image data to identify a plurality of features of at least one eye of a user, and/or for evaluating spatiotemporal fluctuations over time for each of the eye features in real time, and/or for displaying data, optionally in a form of a pattern one or more of: spatiotemporal fluctuations data, and/or spectral data, and/or mental load data and/or stimuli data.

According to some embodiments of the invention, the eye features may be acquired from one or more eyes of a user and may include one or more of the following:

Saccades—moving of the eyes to a different part of a visual image, may be sudden, rapid movements of the eyes. It may take a certain amount of time to initiate a saccade, that is, from time a stimulus is presented to the eye until the eye starts moving, and an additional amount of time to complete the saccade;

Fixation—relative coordinates of position in space of a gaze. The coordinates may be correlated with semantic information of an object in the gaze position. Semantic data on the object of fixation may be extracted. Real-time analysis of field-of-view (FOV) may be carried out and target objects in the FOV may be tagged. Based on the gaze position, extraction of the viewed object may be defined;

Duration of fixation—the time that the gaze is locked on an object as above described. Oscillations of the gaze around an object may be smoothed out and the correlation between the coordinates of point of fixation and semantics/tags may be calculated;

Response time—the time required for eye dynamics to be detectible from onset of stimuli;

Eye transition—collection of data relating to transition period between objects in the FOV and in the objects fixation, e.g., time, velocity and acceleration of the transition period;

Integration—weight of one or more of fixation, duration, response time and eye transition between objects. In addition, one or more further features may be included;

Pupil diameter and/or area variation—changes in diameter and/or area of the ring surrounding the pupil over time, optionally, changes in diameter and/or pupil area due to head movements.

Optionally, blinks may be initiated after onset of one or more of the eye feature.

Additionally or alternatively, each of the features from the user's eye may also be captured and/or identified to provide a baseline mental load for defining a threshold mental load level associated with at least one reference stimulus, e.g., before onset of a stimulus and/or during a stimulus having a generally low mental load level (for example, a relaxing video).

Some embodiments of some aspects of the invention provide methods and systems that do not require calibration and/or a pre-calibration step, e.g., when a user's head may have movement freedom in a predefined space during eye monitoring.

Some embodiments of some aspects of the invention utilize at least one imaging device for monitoring a plurality of eye features from a user's eye(s). Each of the eye features may be monitored while the user is undergoing a physiological-responsive stimulus (e.g., by positioning the imaging device in front of a user with a camera appropriately aimed at the user's eye(s)). Imaging devices that may be utilized according to some embodiments of the invention, include a hardware device comprising a camera such as a mobile device (e.g., a smartphone, a tablet and/or the like), a web camera, a depth camera, an eye tracker, an IR source and/or any eye-monitoring or eye-movement tracking methods and/or devices known in the art for capturing fluctuations in eye image data, optionally, with remote connectivity to a computing device, including a PC, a mobile device, such as, a smart phone, a tablet and/or the like. The imaging device may monitor, optionally simultaneously, one or more of the eye features continuously and/or periodically and/or upon onset and/or transition of a stimuli. Image data of eye features is captured by the imaging system (e.g., a camera) over time. Then, the data is recorded and transmitted to a processor for processing the image data, e.g., via a wireless connection.

In some embodiments, the at least one imaging device may be utilized for capturing image data from the eyes of the user and for monitoring fluctuations in eye features (e.g., by utilizing a video camera installed in a hardware device, such as a mobile device or laptop), and may also be utilized to analyse the image data (e.g., by a software application installed on the hardware device). Additionally or alternatively, in some exemplary embodiments, the imaging device may also provide the stimulus (e.g., a video or images), and may optionally also record output from the user in response to each stimuli (e.g., recording the user's answer to a mathematical question via a microphone).

Image data of one or more of the eye features (e.g., position of the eyes in a space relative to the position of the imaging device) can be recorded from a predetermined distance from the imaging device. After inducing onset of the stimuli, a plurality of features of at least one eye of a user while the user is undergoing the stimulus is monitored and image data of each of the eye features is captured over time. The collection of eye data may be executed continuously and/or periodically and/or upon onset of a stimulus, from a user's right eye and/or left eye, and/or combinations thereof. For instance, the imaging device may analyze image data of horizontal and vertical radii of both eyes, changes in position and/or time of the pupils, and/or relations between the pupils such as desynchronization in position and/or time between the pupils.

The image data may be obtained while the stimulus is undergoing changes over time and at a plurality of time intervals. Each of the time intervals may extend for a time course, for example, between about 10 sec and about 60 sec, or between about 20 sec and about 40 sec. Optionally, a response time corresponding to a time delay between onset of capturing each of the eye fluctuations and onset of the stimuli may be between 100 ms and 1 s, or optionally between 100 ms and 800 ms, or between 200 ms and 700 ms, or between 200 ms and 600 ms, or between 200 ms and 500 ms, or between 200 ms and 400 ms.

Various distances between the imaging device and the user's eye may be utilized according to the invention. For instance, the monitoring eye features and/or the capturing image data may be carried out from far distances, such as from 30 cm to 150 cm, to very short distances, such as, a frame of glasses comprising a camera attached thereto and positioned near the eyes of a user. Optionally, the distance may be between about 1 cm and about 500 cm, or between 1 cm and about 10 cm.

As above mentioned, mental load pupil analysis based on pupil dilation (PD), may include increased noise due to effects of light on dilation of the pupil, thus resulting in inaccurate analysis and may cause mental load signals to be lost in light signal.

Spatiotemporal fluctuations over time in the eye features may be analyzed to transform the data from a time domain to a frequency domain, to thereby provide power density spectra 50 comprising a first spectral pattern 50a for a first frequency range and a second spectral pattern 50b for a second frequency range. In some embodiments, the first frequency range may be between about 0.02 Hz and about 0.3 Hz, or between about 0.03 Hz and about 0.15 Hz, or between about 0.04 Hz and about 0.15 Hz. Additionally or alternatively, in some embodiments, the second frequency range may be between about 0.3 Hz and about 1 Hz, or between about 0.15 Hz and about 0.80 Hz, or between about 0.15 Hz and about 0.50 Hz. Some embodiments of some aspects of the present invention utilize spectral patterns (power density spectra (PSD)) and analysis 40, 50 to advantageously generate a mental load index of a user 60, in real time and with high accuracy.

Some embodiments of some aspects of the invention utilize unique data processing algorithms and/or techniques for one or more of the data processing and/or analysing steps 30-80, including, for example, one or more of: Fourier Function Transforms (FT), Discrete Fourier Transform (DFT), clustering algorithm (e.g., by identifying higher similarities between data points in each cluster compared to similarities in different clusters), changes in eye blinks, blink cleaning algorithms (e.g., Hampel filter), artifacts removal, wavelet denoising, regression, smoothing algorithm, Kalman filtering, Prime-Factor FFT (e.g., for calculating PSD), Multi-Taper Tomson's method (e.g., for calculating PSD), and Detrended Fluctuation Analysis (e.g., DFA-2 with order of 2), etc. In some embodiments, one or more of analysing data and/or generating mental load comprises one or more of the techniques: artifacts removal, denoising, smoothing and Fourier Function Transforms (FFT).

Alternatively or additionally, some embodiments of the invention utilize artifacts removal carried out by one or more data processing techniques and/or algorithms comprising: data filtering algorithm and data validation of pupil fluctuations, to remove noise, such as noise induced from blinks. This may be advantageous, for instance, during eye blinks when an eye lid covers the eye, and a camera may not be able to properly detect the pupil, which may result in loss of information. The Inventors have developed a unique artifacts removal method that interpolates the data linearly and reduces noise, e.g., by removing eye blinks, compensating for the eye blinks, identifying outliers and applying high/low pass filters (determined according to some embodiments of the invention).

Figures 4A, 4B:
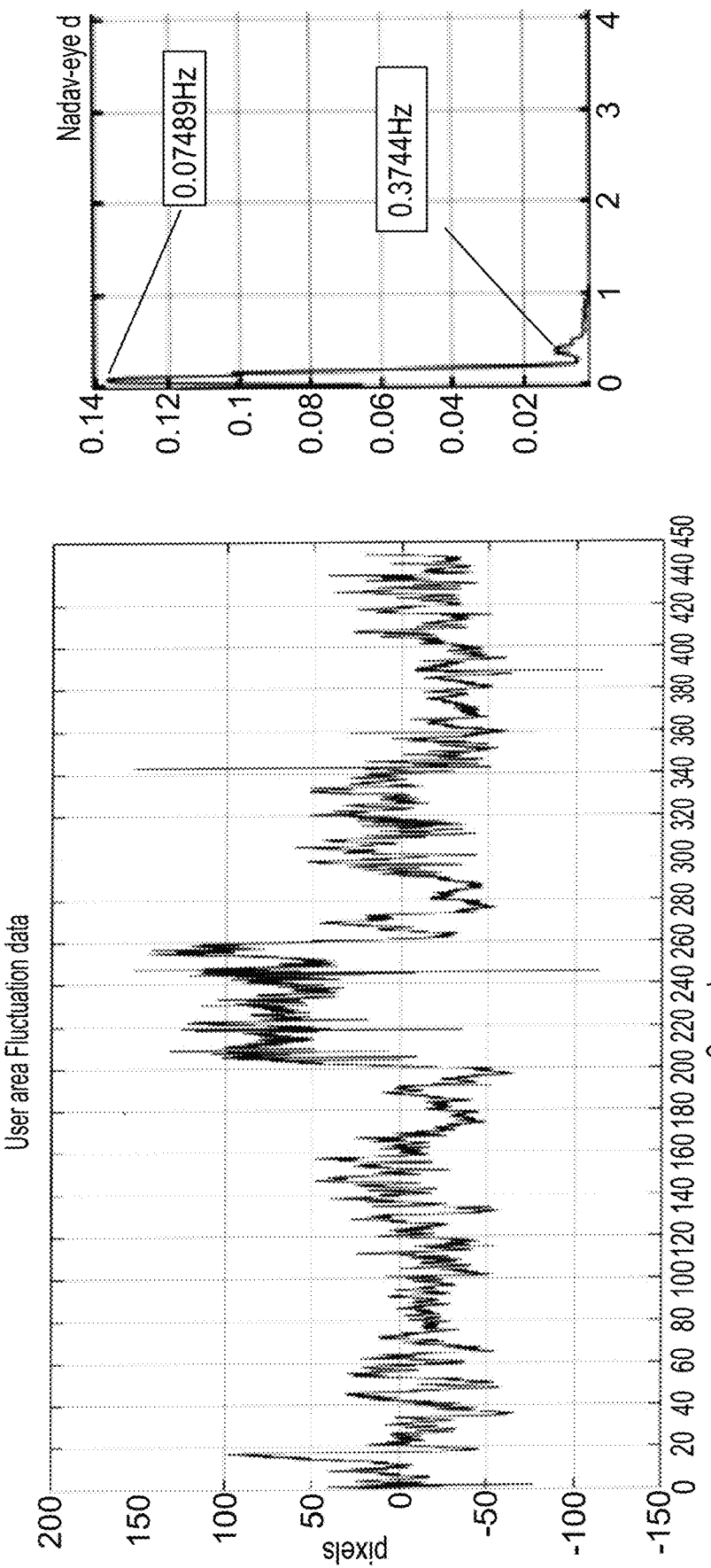
FIG. 4A is a graph showing data output generated from the fluctuations in the eye features recorded, according to FIGS. 3A-B.
FIG. 4B is a graph showing spectral patterns (e.g., power spectrum density graphs) extracted from the data output from the recorded eye fluctuations, according to FIG. 4A.
Figure 5:
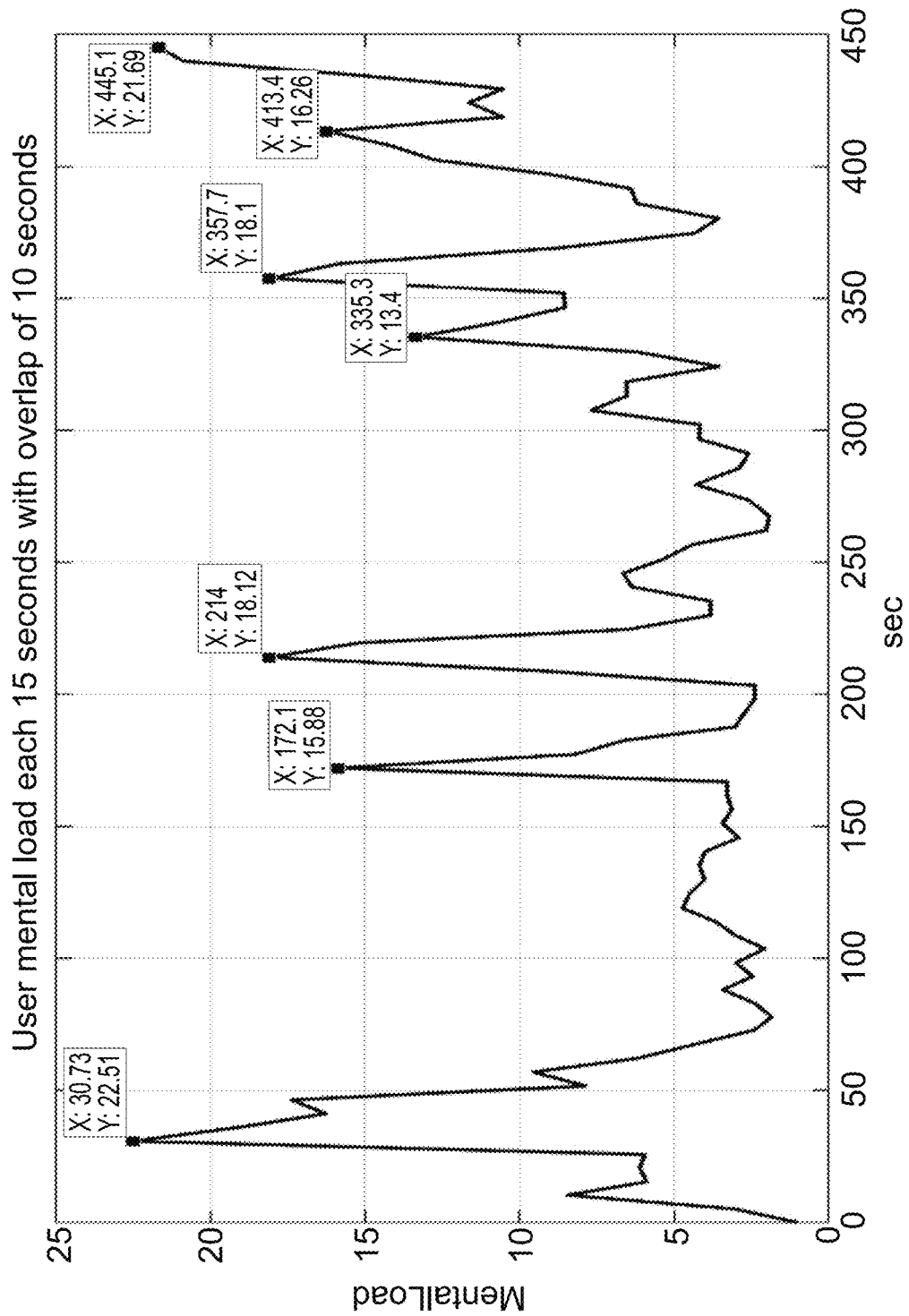
FIG. 5 is a graph showing mental load extraction from the spectral pattern (e.g., power spectrum density graphs), according to FIG. 4B.

Reference is now made to FIGS. 4A-4B, which represent graphs displaying data output generated from a user's pupil fluctuations in response to a stimulus to obtain a temporal signal of the eye's position as a function of time, according to an exemplary embodiment of the invention. Reference is also made to FIG. 5, which represents mental load extraction from the spectral patterns (power density spectra) generated in FIG. 4B.

In the exemplary embodiment shown in FIGS. 4A-4B, artifacts removal has been utilized to remove noise due to eye blinks. FIG. 4B shows a graph displaying power spectrum density (PSD) extracted from the data output from the recorded eye fluctuations of FIG. 4A. FIG. 4B shows that two maxima were applied for calculation of mental load: 0.07489 Hz, and 0.3744 Hz. Mental load output was extracted (e.g., every 15 sec, overlap 10 sec) from FIG. 4B by calculating the ratio between a first frequency (e.g., low frequency 0.04-0.2 Hz) and a second frequency (e.g., high frequency of 0.15-0.6 Hz), as displayed in FIG. 5.

Alternatively, or additionally, in some embodiments the analyzing data and/or generating mental load comprises wavelet denoising (e.g., written by software procedure from Mathlab), such as, contextual tailored denoising mathlab procedure characterized by the following mathematical expression:

$$s(n) = f(n) + \sigma e(n)$$

where s(n) is a N-dimensional random vector (e.g., discrete-time signal with equal time stamps corrupted by additive noise); n=0, 1, 2, ... N−1; e(n) is Gaussian random variables distributed as N(0,1); and variance of the σe(n) is σ2.

Alternatively or additionally, in some embodiments the analyzing data and/or generating mental load comprises employing a moving average Mathlab filtering algorithm, e.g., by smoothing data by replacing each of the first frequency and the second frequency ranges with a predefined average of neighbouring data points within a span to evaluate average intensity of each data point. Some embodiments utilize a mathematical equation including:

$$y_s(i) = 12N + 1(y(i+N) + y(i+N-1) + \ldots + y(i-N))$$

where, ys(i) is the smoothed value of the data point, N is the number of neighboring data points on either side of ys(i), and 2N+1 is the span. The moving average smoothing procedure used by Curve Fitting Toolbox™ follows rules, including:

at least one average smoothing method and/or algorithm selected from:

(i) Fourier Transform Function (FTF) for replacing each data point on each of the first frequency and the second frequency ranges with a predefined average of neighbouring data points to evaluate average intensity of each data point;

(ii) Discrete Fourier transform (DFT) for converting spatiotemporal data indicative of mental response to relative frequency data; and (iii) Prime-factor FFT algorithm for calculating frequency data to provide the power density spectra respective to plurality of ratio patterns of the low frequency and the high frequency ranges.

In some embodiments, the power density spectra are calculated by using Multi-Taper Tomson's method.

In some embodiments, the mental load output(s) is calculated by a ratio, LH, defined by the power spectrum value in a first frequency interval (e.g., 0.05-0.15 Hz, Low Frequency (LF)) divided by the power spectrum value in a second frequency interval (e.g., 0.3-0.8 Hz (HF)).

In some embodiments, each of the mental outputs is characterized by a dependence which comprises a n-base logarithmic relation between a ratio of the first and the second frequencies, wherein n is between 2 and 10. In some embodiments, each of the mental outputs is characterized by a dependence mathematically expressed as $MI = \log_n(LF/HF)$, where MI is the Mental Index (e.g., mental load index), LF is the area bounded by the power density spectrum and the first frequency range axis and the area bounded by the power density spectrum and the second frequency range axis.

Pupil diameter may be highly affected by light flux. Changes in light flux may be a major noise source in extraction of mental load from pupil diameter. The Inventors further found that the methods and systems of the invention are advantageous as the noise associated with light intensity does not essentially affect the measured mental load signal. As such, the methods and systems provided herein provide an accurate and efficient determination of the mental load of a user in response to a stimulus.

Some embodiments of some aspects of the invention provide methods and systems for correlating between a mental state and physiological-responsive stimuli based on a mental load index 208, to classify at least one mental state of a user(s) for each of the time intervals based on the correlation 209.

Extraction of mental load states (e.g., emotions) is based on measures of the mental load index and its behavior over time. Each pair of changes in mental load index and in stimuli readings may be correlated according to a best match (and/or above a defined threshold), to provide accurate classification of each mental state of a user(s).

Reference is now made to FIGS. 6A-6B and FIGS. 7A-7B, which display an example of a process of extraction of mental states according to some embodiments of the invention. Triggers may be correlated the measures of stress/mental load with events. Each event is tagged, which results in a continuous curve that describes the level of mental load (e.g., stress) for each event, providing an ER-ML (e.g., stress), event related mental load.

Figure 6A:
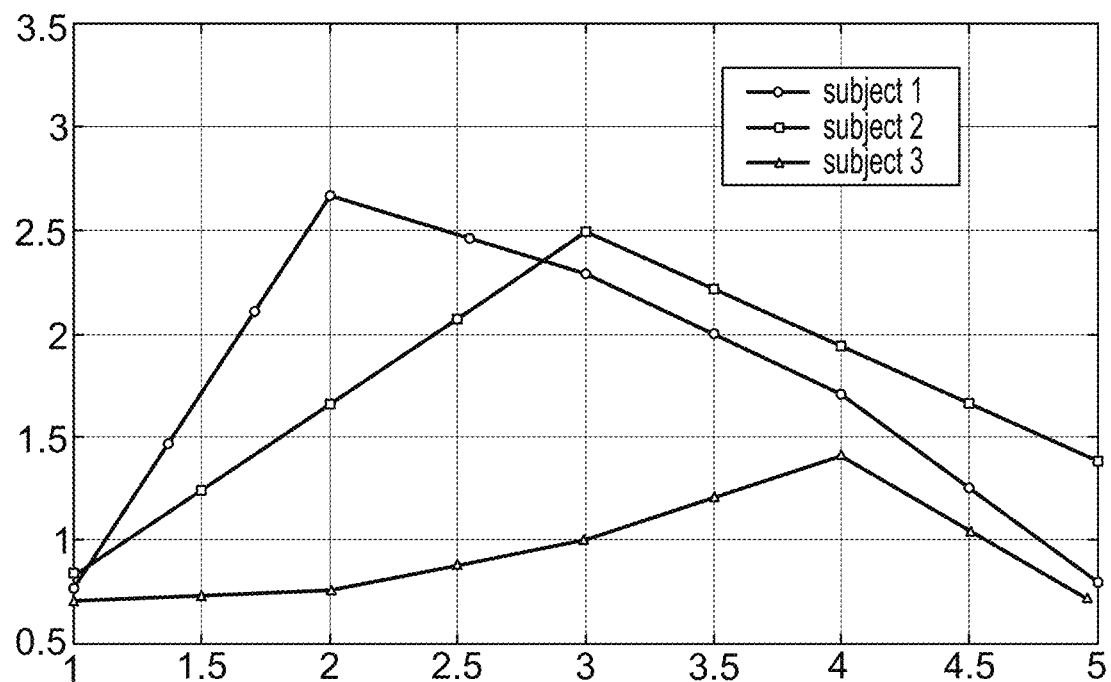
FIGS. 6A-6B are graphs showing an illustration of data output recorded from eye fluctuations in an exemplary experiment showing effects of presenting users with disturbing (6A) and non-disturbing images (6B), according to some embodiments of the present invention.
Figure 6B:
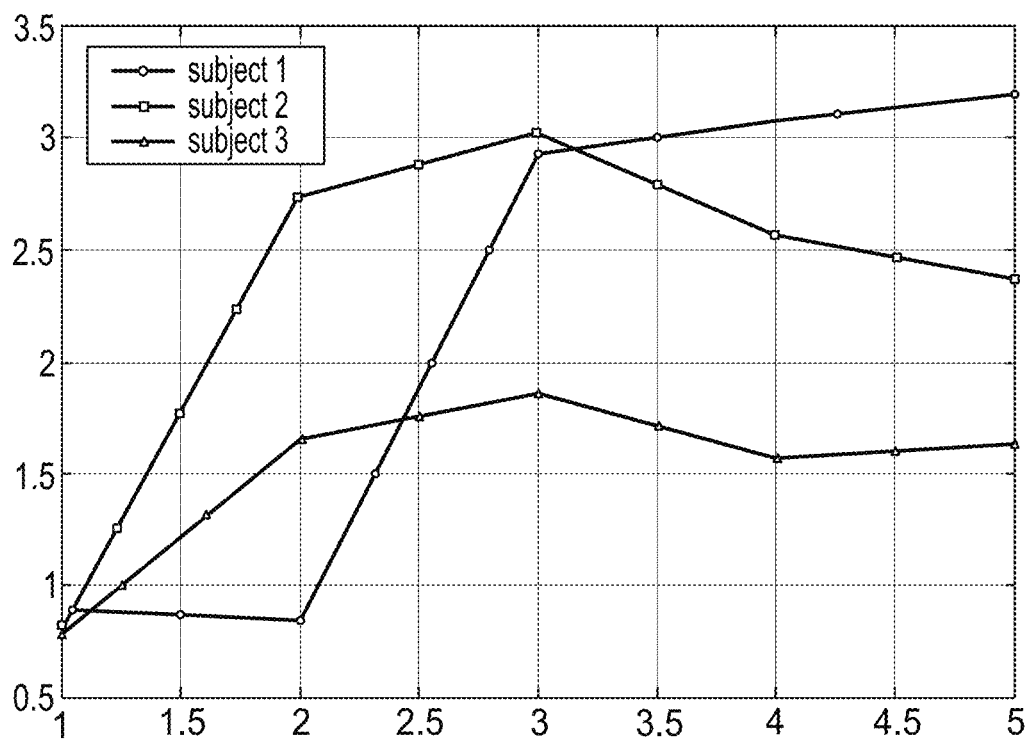
Figure 7A:
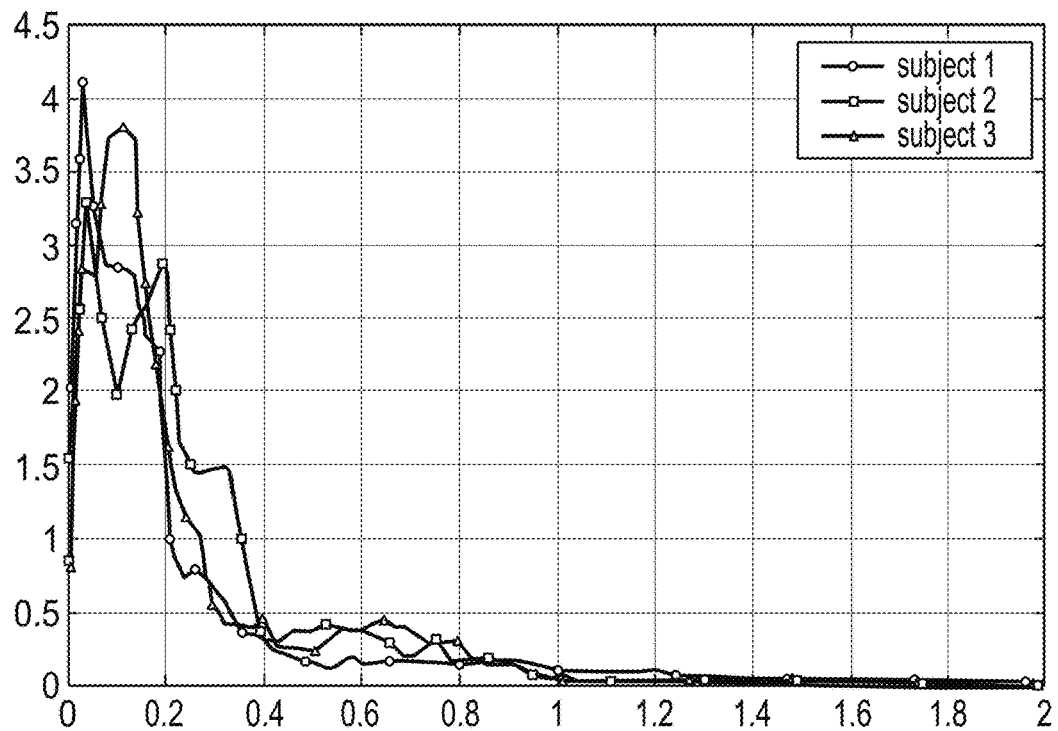
FIGS. 7A-7B are graphs showing corresponding spectral patterns for disturbing images (7A) and for non-disturbing images (7B), according to FIGS. 6A-6B, respectively.
Figure 7B:
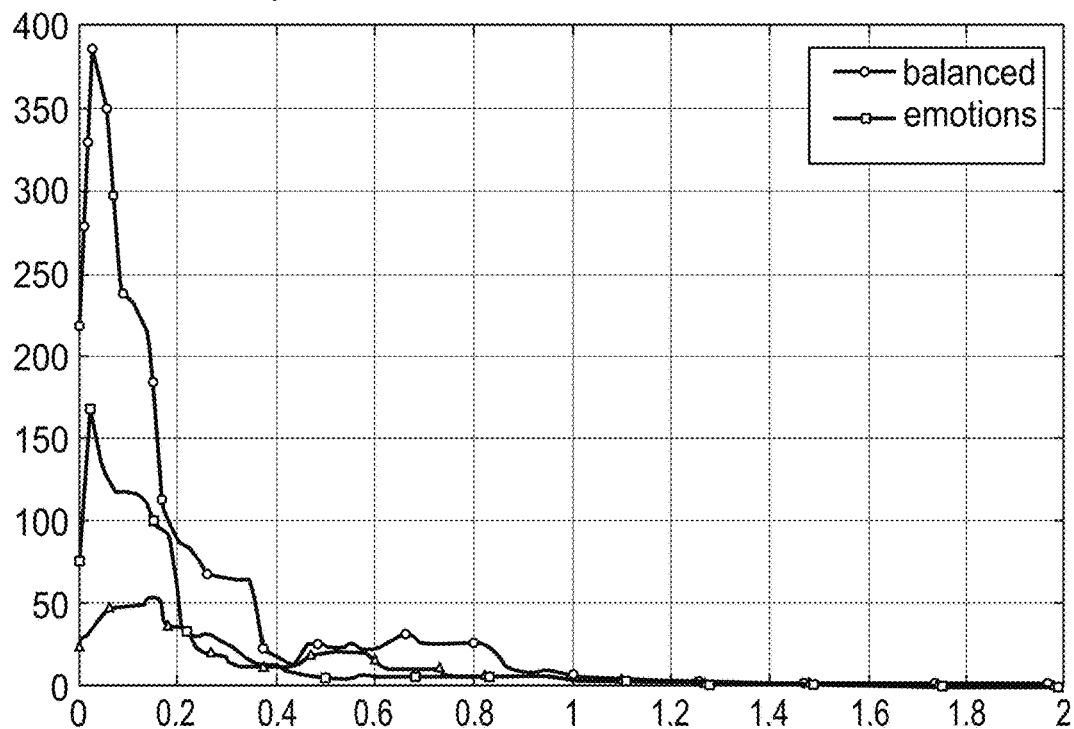

FIG. 6A shows stress extracted from typical eye fluctuation while looking at a relaxing image of people dining of three typical users (measured each 20 sec). FIG. 6B shows stress extracted from eye fluctuation while looking at a disturbing image of animals of three typical users (measured each 20 sec). FIGS. 7A-7B show a power spectrum density while watching the disturbing and non-disturbing images by the same three users, respectively. As shown in FIGS. 6A-6B and FIGS. 7A-7B, the two patterns differ by the dynamics and by the intensity. The relaxed image (FIG. 6A) correlates to a maximum of about 4 units, whereas the right side correlates to at least 5 units (LF/HF, FIG. 6B). In the relaxed case the intensity rises to a peak and then drops. In the right case the participant is holding a high level of stress for a while, then recover, and the stress drops. The responses are an individual character, some which recover fast, some do not recover at all, e.g., remain highly stressed for a while, and some are hardly stressed. Note that the participant indicated by the line containing the triangles, is not highly sensitive, and shows hardly any changes in emotional responses in both cases.

In some additional examples of some embodiments of the invention, in which event-related mental load is measured corresponding to dynamic stimuli, users' responses to a survival nature video was evaluated.

Figure 8A:
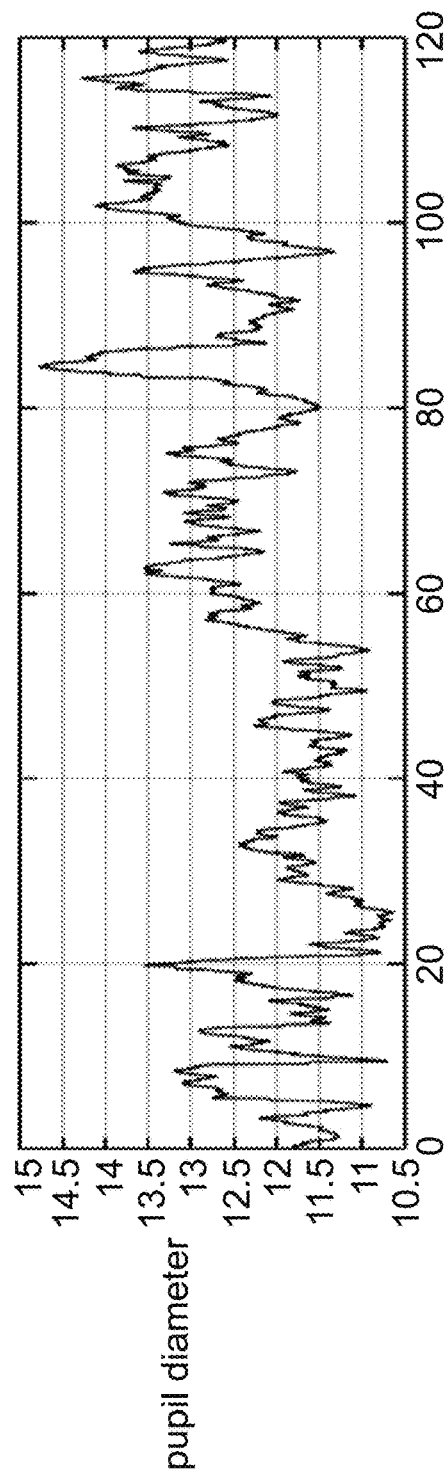
FIGS. 8A-8B are graphs showing an illustration of data output recorded from eye fluctuations in an exemplary experiment showing effects of dynamic perceptual stimuli by presenting users with a video (8A) and the corresponding mental load (8B), according to some embodiments of the present invention.
Figure 8B:
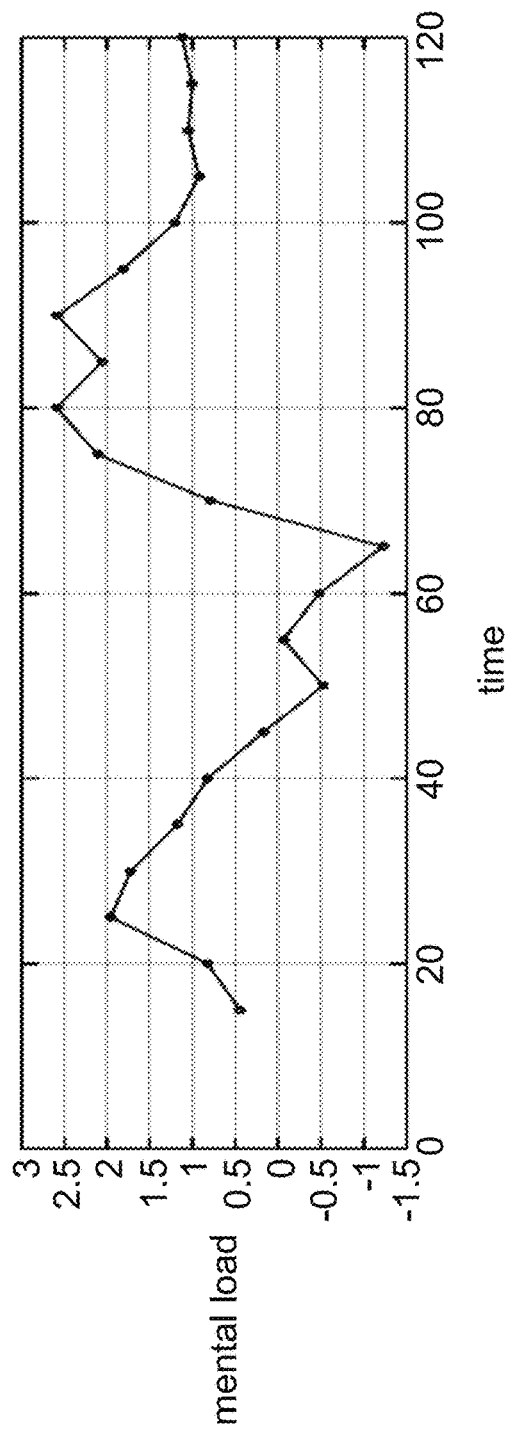

FIGS. 8A-8B are graphs showing mental load extracted from eye fluctuation in a user in an exemplary experiment showing effects of dynamic perceptual stimuli by presenting the user with a video (8A) and the corresponding mental load/stress intensity (8B), according to some embodiments of the present invention.

The length of the video was about 2 minutes. The eyes of the participants were monitored by an eye-tracker SMI RED500, refresh rate of 500 Hz, during watching. The video can be watched at:
https://www(dot)youtube(dot)com/watch?v=B3OjfK0t1XM&feature=youtube.

Pupil fluctuations were recorded and artifacts were removed, according to any of the above techniques (e.g., Multitaper Thompson method, Moving Window Method, filters and/or additional as described above according to some embodiments of the invention). Frequencies were extracted from a power spectrum density chart. The mental load increased with the excitation in the video (e.g., stress level). The measured pupil diameter during the two minutes video is displayed in FIG. 9A, and the mental load extracted from the pupil fluctuations is displayed in FIG. 9B. Properties of this viewer are in the level of excitement which was relative to other viewers, pretty high; the viewer started relatively upset (ML~0.5) and completed watching the video with a stress level higher than the initial.

In some additional examples of some embodiments of the invention, in which event-related mental load is measured corresponding to dynamic cognitive stimuli, users' responses to questions was evaluated.

Figure 9A:
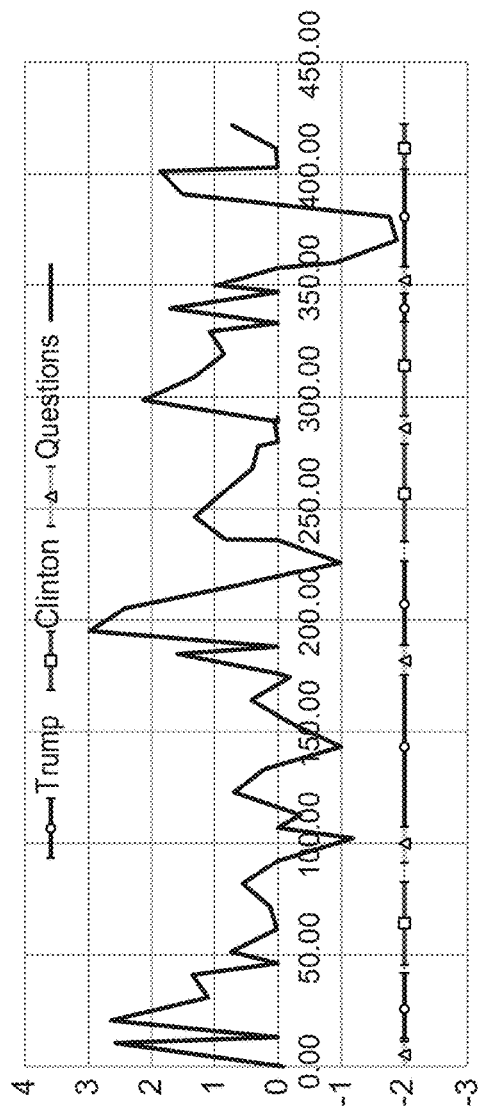
FIGS. 9A-9B are graphs showing mental load extracted from eye fluctuation in a user in an exemplary experiment showing effects of dynamic cognitive stimuli by presenting the user with questions (9A) and the corresponding mental load/stress intensity (9B), according to some embodiments of the present invention.
Figure 9B:
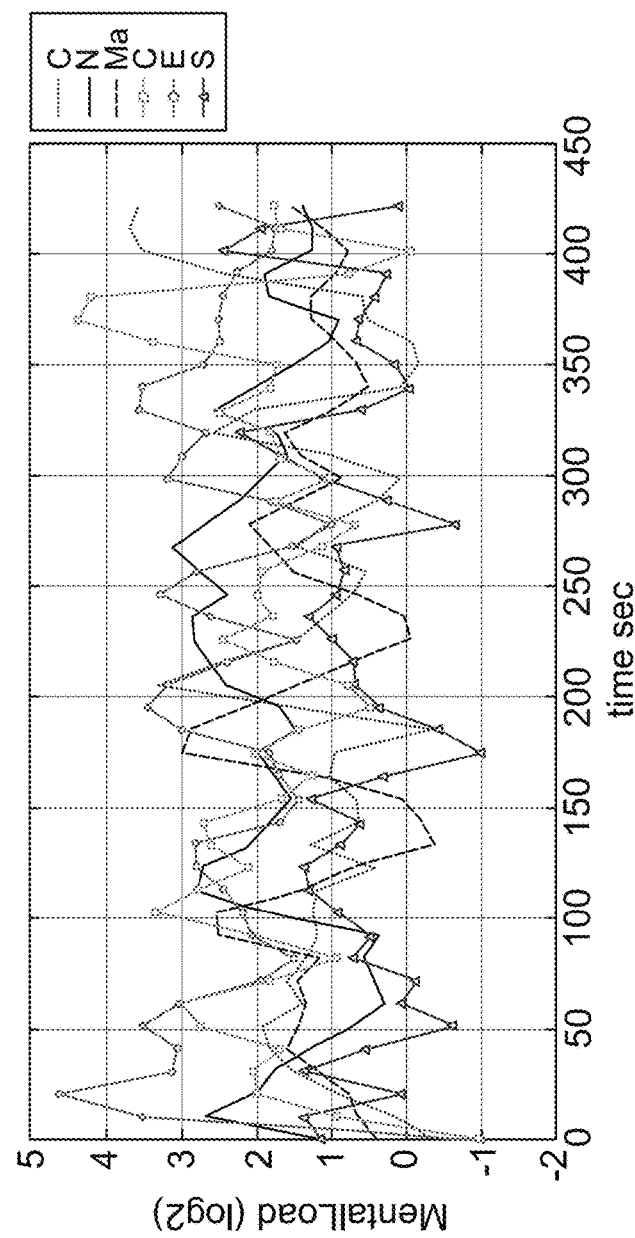

FIGS. 9A-9B are graphs showing mental load extracted from eye fluctuation in a user in an exemplary experiment showing effects of dynamic cognitive stimuli by presenting the user with questions (9A) and the corresponding mental load/stress intensity (9B), according to some embodiments of the present invention. Participants were asked to watch a video of two candidates on their second debate towards presidential elections with real time recording of their eye fluctuations. Four sections were included in the video each describing the work plan on four major questions: taxs; ethics of presidential candidates; judges for the Supreme Court; Clean energy, job opportunity. The full time interval analyzed was ~412 (411.5532) sec. Results of a single user are shown in FIG. 9A. The user shows higher responses to republican candidate and is more relaxed when watching the democrat candidate.

Fuzzy c-mean clustering procedure as described above was used to generate levels of excitation resulting from increase in mental load. Statistical data analysis of ML results of 27 participants showed 4 main levels that correlate with levels of mental load. The first level represents very low mental load (center line, −0.0874), and shows that the participant is bored and barely interested in the video. The second corresponds to 'somewhat interested' (center-line, 08725), the third is highly interested (1.7602) and the last (2.9750) is very high mental load. FIG. 9B illustrates the mental load of nine participants, across time, and for each section of the video (e.g., tax problem, republican response). The intensity of ML/stress in response to each question. For instance, a ML response in the time interval of 350-400 sec was very high. The level of physiological response on each topic, for each candidate, was correlated with the response in an interview. The responses were found consistent.

Figure 10:
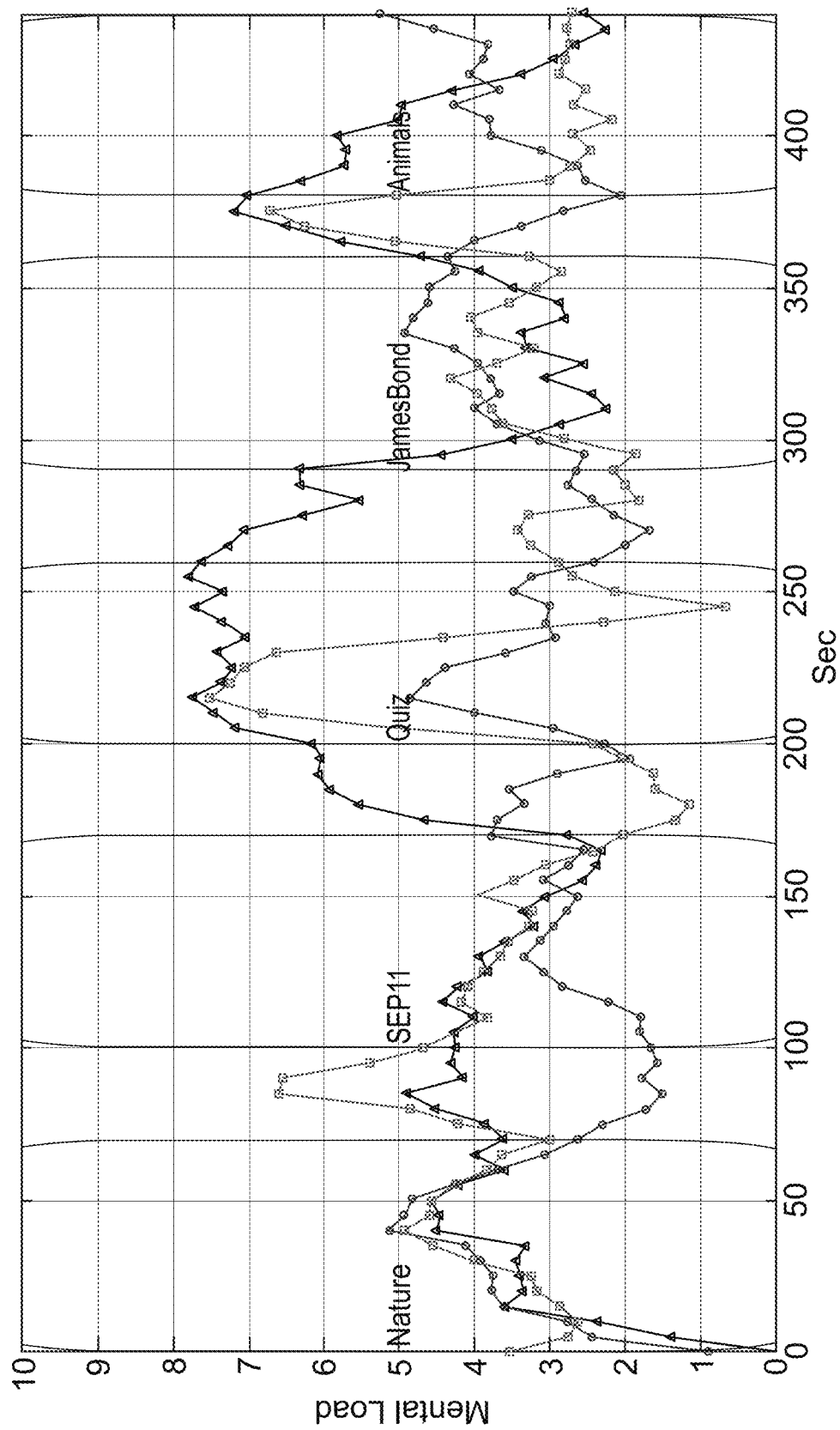
FIG. 10 is a graph showing a profile of tacit political beliefs of each user on each topic according to FIG. 9B.

The method of the invention may utilize clustering algorithm(s) to determine classification levels, e.g., as identified in FIG. 10, which illustrates a profile of political beliefs of each user on each topic according to FIG. 9B. As such, the invention provides an accurate and efficient method for creating an event-related profile of a user. The invention provides a method of classifying and/or predicting at least one mental state of user(s) based on correlation(s) between fluctuations in the mental load index in each of the time intervals corresponding to changes in stimuli over time.

Some embodiments of the present invention provide a system, a method, and/or may implement a computer program (e.g., a software, an application and/or an algorithm), which may include computer readable program instructions for analyzing data relating to eye movement activity recorded using eye tracking devices in a mobile device.

Some embodiments of the present invention can use a mental load index determined according to any of the methods described above, for determining a number of useful indications, including but not limited to: human performance (and/or dynamics) based on the measuring eye features fluctuations; a current mental load of human performance in real-time, e.g. on-line; human proficiency level in simulators and real conditions; interface perfection of a man-machine system; complexity of human controlled procedures; presenting feedback on current mental load in real-time; level of mental, cognitive and regulative processes; diagnosing mental, cognitive and/or emotional states of a user.

Optionally, one or more machine learning techniques and/or algorithms may be applied to learn the mental load outputs of one or more of the users in order to classify at least one mental state of an individual user or a plurality of users in response to a stimulus. The application may evaluate the mental state(s) based on positive and/or negative correlation(s) between fluctuations in the mental load index in each of the time intervals corresponding to changes in the stimuli over time and applying the learned outputs.

It is expected that during the life of a patent maturing from this application many relevant systems, methods and computer programs will be developed and the scope of the terms imaging device and/or camera and/or monitoring and/or tracking device is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The word "exemplary" is used herein to mean "serving as an example, an instance or an illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for controlling in real time a device operated by a user according to mental states determined for the user while operating the device, the method comprising:
   capturing by at least one imaging device image data depicting at least one eye of a user, monitored by said at least one imaging device, while the user is presented with a dynamic physiological-responsive stimuli and during said user operating at least one device;
   in real time, during said user operating said at least one device and conducting by at least one hardware low latency processor:
   analysing the image data to identify a plurality of features of the at least one eye;
   calculating spatiotemporal fluctuations over time for each of the plurality of identified features;
   calculating, based on the spatiotemporal fluctuations, a plurality of spectral patterns having a first frequency and a second frequency;
   calculating a plurality of mental load patterns based on a ratio between the spectral patterns of the first and second frequencies in a plurality of time intervals corresponding to changes in a level of the stimuli;
   correlating between each of the plurality of mental load patterns and the stimuli level in each of the plurality of time intervals;
   defining, based on the correlation, a mental load index of the user by comparing each of the mental load patterns to a plurality of thresholds each defining a respective one of plurality of mental states;
   determining in real-time, during said user operating said at least one device, a mental state of the user based on the mental load index by analysing the spatiotemporal fluctuations identified in real-time image data responsive to a plurality of stimuli;
   generating an output indicative of said determined mental state of the user;
   transmitting said output from said at least one low latency processor to a hardware system controller over a communication network; and
   according to said output received by said controller, selectively restricting an access to a particular task and/or to the at least one device operated by the user according during the user operating said at least one device.

2. The method according to claim 1, wherein the plurality of features is at least one of: fixation, duration of fixation, response time, saccades and microsaccades characteristics, latency in saccade/microsaccades response to stimuli, eye dynamics, pupil diameter and/or area variation, blink duration and blink rate.

3. The method according to claim 1, wherein the calculating spatiotemporal fluctuations step comprises integrating weight corresponding to at least one of the plurality of features selected from: fixation, saccade characteristics, saccade response time, duration, drift and response time of drift.

4. The method according to claim 1, wherein the image data is obtained by an imaging device selected from: a camera, smartphone, eye tracker and sonic source.

5. The method according to claim 1, wherein the image data is obtained from a distance between the imaging device and the user's eye of between about 1 cm and about 500 cm.

6. The method according to claim 1, wherein the distance is between about 1 cm and about 10 cm.

7. The method according to claim 1, wherein the calculating spectral patterns step comprises at least one analysis technique or algorithm selected from: clustering algorithm, changes in eye blinks, artifacts removal, wavelet denoising, regression, smoothing algorithm, Fourier Transform Function (FTF) and Kalman filtering.

8. The method according to claim 7, wherein the artifacts removal is carried out by at least one of data filtering algorithm and data validation.

9. The method according to claim 1, wherein the spatiotemporal fluctuations are further analysed by at least one average smoothing method and/or algorithm selected from:
   (i) Fourier Transform Function (FTF) for replacing each data point on each of the first frequency and the second frequency with a predefined average of neighbouring data points to evaluate average intensity of each data point;
   (ii) Discrete Fourier transform (DFT) for converting spatiotemporal data to relative frequency data; and
   (iii) Prime-factor FFT algorithm for calculating frequency data to provide spectral patterns respective to the plurality of ratio patterns of the first frequency and the second frequency.

10. The method according to claim 1, wherein the identifying a correlation step comprises assigning each point on each of the spectral patterns to at least one cluster based on similarity features to other points in the spectral patterns selected from: distance, connectivity, intensity characteristics and duration.

11. The method according to claim 10, wherein the assigning each point to at least one cluster comprises fuzzy c-mean clustering.

12. The method according to claim 1, wherein the calculating the mental load pattern is carried out at time intervals of between about 10 sec and about 60 sec.

13. The method according to claim 1, wherein the time intervals are between about 20 sec and about 40 sec.

14. The method according to claim 1, wherein the first frequency is between about 0.02 Hz and about 0.3 Hz and second frequency is between about 0.3 Hz and about 1 Hz.

15. The method according to claim 1, wherein the first frequency is between about 0.03 Hz and about 0.15 Hz.

16. The method according to claim 1, wherein the first frequency is between about 0.04 Hz and about 0.15 Hz.

17. The method according to claim 1, wherein the second frequency is between about 0.15 Hz and about 0.80 Hz.

18. The method according to claim 1, wherein the second frequency is between about 0.15 Hz and about 0.50 Hz.

19. The method according to claim 1, wherein each of the mental load patterns is characterized by a dependence which comprises a n-base logarithmic relation between a ratio of the first and the second frequencies, wherein n is between 2 and 10.

20. The method according to claim 1, wherein each of the mental load patterns is characterized by a dependence mathematically expressed as $MI=\log_n(LF/HF)$, where MI is the Mental Index, LF is the area bounded by the spectral pattern and axis of the first frequency and the area bounded by the spectral pattern and axis of the second frequency axis.

21. The method according to claim 1, wherein the stimuli comprising at least one of: queries provided to a user by a virtual agent, and/or an interactive agent and/or a video.

22. The method according to claim 1, wherein the determining of the mental load index is by comparing a mental load pattern in a first time duration to a baseline mental load having a threshold corresponding to another time duration characterized by presenting no stimuli or a generally low responsive stimuli to a user.

23. The method according to claim 1, wherein the step of identifying a correlation comprises identifying one or more of a start time, an end time or a time duration of each of the plurality of time interval corresponding to changes in the level of the of stimuli.

24. The method according to claim 23, wherein the identifying of one or more of the start time, end time and time duration of each of the plurality of time interval corresponding to changes in the level of the stimuli is based on obtaining an emotional feedback from a user to each stimuli.

25. The method according to claim 24, wherein the obtaining the feedback is by recording the user's output to mental load level respective to each of the stimuli by one or more of the techniques: a questionnaire comprising feedback questions, heart rate variability (HRV), heart rate (HR), galvanic skin response (GSR), changes in frequencies of facial colors, and EEG.

26. The method according to claim 1, further comprising using the mental load index as a feedback for training to determine a mental state of a user in response to a stimuli by correlating between the trained feedback mental load and the mental load of the user.

27. The method according to claim 1, wherein the method does not include a calibration step.

28. The method according to claim 1, further comprising calculating changes in response time of the user to each of the plurality of stimuli.

29. The method according to claim 1, wherein the mental state comprising one of: disengaged, calm, interested, and stressed.

30. A system for controlling in real time an operation of a device operated by a user according mental states determined for the user while operating the device, the system comprising:
   at least one imaging device monitoring at least one eye of a user for by capturing image data while the user is presented with a dynamic physiological-responsive stimuli and during said user operating at least one device;
   a hardware system controller; and
   at least one low latency processor for conducting in real time, during said user operating said at least one device:
      receiving the image data from the at least one imaging device;
      analysing the image data to identify a plurality of features of the at least one eye;
      calculating spatiotemporal fluctuations over time for each of the plurality of identified features;
      calculating, based on the plurality of identified features, spatiotemporal fluctuations over time for each of the plurality of identified features;
      calculating, based on the spatiotemporal fluctuations, a plurality of spectral patterns having a first frequency and a second frequency;
      calculating a plurality of mental load patterns based on a ratio between the spectral patterns of the first and second frequencies in a plurality of time intervals corresponding to changes in a level of the stimuli;
      correlating between the mental load patterns and the stimuli level in each of the plurality of time intervals;
      defining, based on the correlation, a mental load index of the user by comparing each of the mental load patterns to a threshold respective to a plurality of mental states;
      determining in real-time, during said user operating said at least one device, a mental state of the user based on the mental load index by analysing the spatiotemporal fluctuations identified in real-time image data responsive to a plurality of stimuli;
      generating an output indicative of said determined mental state of the user; and
      transmitting said output to said hardware system controller over a communication network;

wherein said hardware system controller is configured to receive said transmitted output and according to said output, selectively restrict an access to a particular task and/or to the at least one device operated by the user during the user operating said at least one device.

31. The system according to claim 30, wherein the at least one imaging device is selected from: a camera, a TV, a mobile device, an eye tracker, an IR source, and a sonic source.

32. The system according to claim 30, further comprising a display for displaying data obtained from the processor.

33. The system according to claim 30, further comprising a classifier for classifying at least one mental state based on comparing the mental load index obtained from the processor, to stored mental load data.

34. The system according to claim 33, wherein the imaging device and the processor, and optionally, one or more of the display, the controller and the classifier are embedded in a single device.

* * * * *